| United States Patent [19] | [11] | 4,374,120 |
|---|---|---|
| Soini et al. | [45] | Feb. 15, 1983 |

[54] FLUORESCENCE SPECTROSCOPY ASSAY MEANS WITH FLUORESCENT CHELATE OF A LANTHANIDE

[75] Inventors: Erkki Soini; Ilkka Hemmilä, both of Turku, Finland

[73] Assignee: Wallac Oy, Turku, Finland

[21] Appl. No.: 128,621

[22] Filed: Mar. 7, 1980

[30] Foreign Application Priority Data

Mar. 8, 1979 [SE] Sweden ................................ 7902079

[51] Int. Cl.$^3$ ..................... G01N 21/33; G01N 33/48; G01N 33/52
[52] U.S. Cl. .................................. 436/546; 250/305; 250/461.2; 435/7; 435/35; 436/800; 436/547; 424/7.1
[58] Field of Search ............................ 424/7, 8, 12, 13; 23/230 B; 250/305, 461.2; 435/7, 35

[56] References Cited

U.S. PATENT DOCUMENTS

| 4,058,732 | 11/1977 | Wieder | 250/461 B |
| 4,133,873 | 1/1979 | Noller | 23/230 B |
| 4,259,313 | 3/1981 | Frank | 424/7 X |

OTHER PUBLICATIONS

Zheltvai et al., Koordinatsionnaia Khimiia, vol. 2, 1976, pp. 1600–1608.
Moller et al., Chem. Rev., vol. 65, 1965, p. 1.
Makhijani et al., J. Ind. Chem. Soc., vol. 60, 1978, p. 840.
Nakatani et al., Rev. Phys. Chem., Japan, vol. 42, 1972, p. 103.
Polmektov et al., Zh. Neorg. Khim, vol. 19, 1974, p. 3257.
Wieder, Chem Abs, vol. 90, 1979 (citing Immunoflouresc Tech. Proc. Int. Conf. 6th, 1978, p. 67–80).
Leung, Biochem & Biophys. Res. Comm. vol. 75, No. 1, 1977, pp. 149–155.

*Primary Examiner*—Anna P. Fagelson
*Attorney, Agent, or Firm*—Fisher, Christen & Sabol

[57] ABSTRACT

An improved method of determining the nature of a substance by fluoroscence spectroscopy wherein a fluorescent marker is coupled to the molecules of the substance comprises the use of a marker having a longer period of fluorescence than those of possible sources of noise and by employing an exciting radiation pulse of short duration so that the fluorescence of the marker is detected after the objectionable sources of fluorescence have ceased; the marker including a fluorescent lanthanide chelate complex.

18 Claims, No Drawings

FLUORESCENCE SPECTROSCOPY ASSAY MEANS WITH FLUORESCENT CHELATE OF A LANTHANIDE

The present invention refers to a method for determining of a substance by means of fluorescence spectroscopy in which a fluorescent marker is coupled to the molecules of the substance, the fluorescence of the marker having a duration which substantially exceeds the duration of the fluorescence of possible noise sources and in which the substance is excited by means of a short pulse of radiation and the fluorescence thereby generated is detected when the fluorescence from the sources of noise has in principle ceased.

In fluorescence spectroscopy the substance to be determined which is present in a liquid or a solid phase is subject to a radiation with a known spectral distribution, for instance light with a limited band width. The fluorescent radiation thereby emitted has a longer wavelength than the exciting radiation and is specific for the substance to be determined. The intensity of the fluorescent radiation is measured and constitutes a measure of the quantity of the substance to be determined.

A disadvantage of the spectrofluorimeters presently used is that their sensitivity is limited due to noise in the exciting and detecting systems and furthermore disturbing fluorescence is generated from other substances such as substrate material, sample holders, air particles, other fluorescent substances in the sample, in reagents etc.

A specific problem in fluorescent determinations within immunology is that serum has a relatively strong fluorescence which gives rise to high background levels for most fluorescent markers. This fluorescence in serum derives mainly from different proteins which however have relatively short excitation and emission wavelength (excitation maximum at 280 nm, emission maximum at 330–340 nm) and this fluorescence is not a more substantial source of noise. However, in serum also other types of fluorescence is obtained, this fluorescence presumably deriving from other compounds than proteins and appearing at longer wavelengths (excitation at 340 nm, emission at 460–470 nm) and therefore gives rise to more complicated disturbing phenomena. In addition to the fluorescence of serum the background is affected by a heavy scattering. The scattering gives rise to an interference, especially when markers with a small Stoke's shift (less than 50 nm) are used. Because of a high background fluorescence and this scattering the sensitivity of markers in a sample containing serum is reduced by 50–100 times as compared to the use of the same markers in a pure buffer.

The demands put on a marker used in immunological systems are that it should have the highest possible fluorescence, a relatively long emission wavelength (more than 500 nm), a high Stoke's shift and a possibility to be bound covalently to the antibody or the antigen without negatively affecting the conjugation properties.

The organic markers used in biological systems, for instance fluoresceinisothiocyanate (FITC), rhodamines(RBITC, TRITC, RB-200-SC), dansil chloride (DNS-Cl), fluorescamine (FL) etc. give a rather strong fluorescence. They are bound covalently to the antibody/antigen and are relatively stable. Nevertheless, their use is limited by the background fluorescence. Many of them have a fluorescence in the same wavelength range as serum and many of them are heavily affected by the scattering. The sensitivity when using these markers can be increased by a development of the method, for instance by using a solid state system or by development of the instrumentation used. In fluorescent determinations for instance within immunology the substance to be determined is provided with a fluorescent marker which has a relatively long fluorescent time as compared to the fluorescence of surrounding substances. Furthermore, the material to be determined is separated from other substances by means of techniques known per se, such as chromatography or antibody binding. An instrument system suitable for this purpose is shown in the U.S. Pat. No. 4,058,732 (Wieder) which describes a device where the sample is excited by a laser pulse and where the marker is a substance with a fluorescence having a duration considerably exceeding the duration of the fluorescence of the noise sources. When the laser pulse has excited the sample the detection takes place only when a sufficiently long time has passed for the fluorescence from the noise sources to have decayed. It turns out that the markers described in this patent are not suitable for commercial use. Thus, they are for instance very sensitive for dilution.

It is an object of the present invention to provide a method which by using the above instrumentations forms a well functioning system by choosing markers adapted to the system. The characteristics of the invention appears from the claims attached to the specification.

The fluorescence properties of certain lanthanide chelates, especially chelates of europium and terbium, are well suited fluorescent markers. The absorbance of these chelates is very strong, (more than $10^4$) and dependent upon the ligands. Although the quantum yield is often smaller than that for organic markers these chelates have other advantages, thus the emission appears at relatively long wavelengths (terbium 544 nm, europium 613 nm) in which wavelength range the serum fluorescence is low and furthermore the excitation maximum is within the short UV-range (Terbium-chelates 270–320 nm, Eu-chelates 320–360 nm) independent of the ligands which makes it possible to excite them with lamps or lasers commercially available and furthermore the Stoke's shift is very long (240–270 nm) and the emission band is sharply limited which enables a small band width. The most essential property is however that the fluorescence time is long, about 50–1000 microseconds which makes it possible to use the above mentioned instrumentation. As the fluorescence is measured with a certain delay during which the background fluorescence has decayed, the effect of an unspecific background radiation can be eliminated.

The chelates of europium and to a certain extent terbium together with different β-diketones are the most used chelates due to their ability to laser in different solutions and at different temperatures. The most widely used β-diketones are benzoylacetone (BA), dibenzoylmetane (DBM), thenoyltrifluoroacetone (TTA), benzoyltrifluoroacetone (BTA), 1- and 2-naphihoyltrifluoroacetone (1-/2-NTA), acetylaceton (AcA), trifluoroacetylacetone (TFAcA), and hexafluoroacetylacetone (HFAcA). In addition to β-diketones the lasering properties of different salicylate chelates have previously been investigated and different methods for fluorometric determination of lanthanide ions (Eu, Tb, Sm, Dy) has been developed using these compounds and other ligands, such as terbium with dipicolinic acid (DPA) and with EDTA and sulphosalicyl acid (SSA). Under favourable conditions the quant yield of these chelates can be very high and come close to 100 percent.

The strong fluorescence of the lanthanide chelates is due to the absorption by the ligands of the excitation radiation and of the energy transfer from the triplet state of the ligand which gives rise to a narrow band radiation with a long wavelength characteristic for metals.

Before a chelate of the above mentioned type could be used as a fluorescent marker it has to be attached to the antibody/antigen to be investigated. Furthermore, the metal has to give a fluorescent radiation also after the binding and in a water solution. To be stable enough, also in very diluted form (even below $10^9 M$) and under conditions where other chelate forming reagents are present as well as an excess of other metal ions, the binding system must be very strong. The stability constant of the chelate must be well above $10^{10}$ and additionally the binding ligand has to leave coordination positions free for another bidentate ligand. When the metal is bound with β-diketone analogues the stability is not sufficient in diluted systems. The stability constants for β-diketonates, for instance acetylacetone with europium, $K_1$, $K_2$ and $K_3$ and $10^{5.87}$, $10^{4.48}$ and $10^{3.29}$, respectively, which is not high enough. In micro molar concentrations such tris- or tetrakischelates are dissolved and do not give any fluorescent radiation.

An example of chelate forming reagents having a sufficient stability for this purpose are aminopolycarboxyl acids, especially EDTA, HEDTA, and other 5 - 6 dentate complex formers. They furthermore permit one β-diketone to be bound to the metal ion although with a decreased stability. The aminopolycarboxylic acids used as a secondary ligand in many fluorometric determination systems to determine trace amounts of lanthanides in water solutions.

In a fluorescence immuno determination system an analogue of the above mentioned complex formers could be used if it is provided with a suitable functional group by means of which it can be bound to the antigen-/antibody. An example of such a bi-functional ligand is 1-(p-diazonium phenyl)-ethylenediaminetetraacetic acid. It has previously been used for marking of protein with radio active metals and has also been used for binding fluorescent metals such as terbium and europium to proteins in order to study protein structures.

In fluoro immunoassay systems the europium or terbium ion could be bound to the antibody/antigen or a haptenic molecule via an aminopolycarboxylic acid analogue (EDTA-analogue, HEDTA-analogue, etc.). After the binding the 1:1:1 chelate could be formed with a β-diketone and kept stable at an equilibrium by supply of sufficent excess of the β-diketone. The required excess can be calculated from the stability constants or could be experimentally titrated with the β-diketone by means of studies of the increasing fluorescence. The affinity for a second β-diketone to the metal is not sufficient to dominate the aminocarboxylate even in an excess of several powers of ten. Therefore the β-diketone could be used in a great excess. Too high concentrations only imply a limitation of the optical absorbance. The β-diketone will namely give rise to a high absorption and therefore attenuates the excitation.

A fluoro immunoanalysis system according to the invention will thus consist of a haptene, an antigen or an antibody with an europium or a terbium marker, whereby the metal is bound via an aminopolycarboxylic acid analogue (EDTA-analogue or HEDTA-analogue). The other ligand can be a β-diketone (TTA, BTA, HFAcA, AcA, 1/2-NTA) or a dihydroxy compound (for instance sulphosalicylic acid, TIRON (a registered trademark for the disodium salt of 3,5 pyrocatecholdisulfonic acid), 2,3-dihydroxynaphthalene, 2,3-dihydroxynaphthalene sulfonyl acid derivative etc.). The system can also contain a solid phase or some other separation system or the fluorescense could be attenuated or developed in an immuno reaction. In a system where the sensitivity of a fluorometer is not sufficient, the sensitivity can be increased by means of a time resolving instrument.

We claim:

1. In a method for the determination of a substance by means of fluorescence spectroscopy in which a fluorescence marker is coupled to the molecules of the substance, the fluorescence of the marker having a duration which substantially exceeds the duration of the fluorescence of possible noise sources and in which the substance is excited by means of a short pulse of radiation and the fluorescence thereby generated is detected when the fluorescence from the sources of noise has in principle ceased, the improvement comprising using as said fluorescent marker a 1:1:1 fluorescent chelate of europium or terbium, β-diketone or a dihydroxy compound, and an aminopolycarboxylic acid analogue, said chelate having a stability constant above $10^{10}$ wherein
   (a) the europium or terbium is the fluorescence emission source and is chelated to the aminopolycarboxylic acid analogue,
   (b) the aminopolycarboxylic acid analogue has a functional group for covalent binding to said substance, and
   (c) said β-diketone or said dihydroxy compound excites fluorescence of said fluorescence emission source.

2. Method according to claim 1 wherein the fluorescence emission source is europium.

3. Method according to claim 1 wherein the fluorescence emission source is terbium.

4. Method according to claim 1, wherein the aminocarboxylic acid analogue is an EDTA-analogue.

5. Method according to claim 1, wherein the aminocarboxylic acid analogue is a HEDTA-analogue.

6. Method according to claim 1, wherein said substance comprises hapten.

7. Method according to claim 1, wherein said substance comprises an antibody.

8. Method according to claim 1, wherein said substance comprises an antigen.

9. Method according to claim 1 wherein said β-diketone is selected from the group consisting of benzoylacetone, dibenzoylmethane, thenoyltrifluoroacetone, benzoyltrifluoroacetone, 1- and 2- naphthoyltrifluoroacetone, acetylacetone, trifluoroacetylacetone, and hexafluoroacetylacetone, said dihydroxy compound is selected from the group consisting of sulphosalicylic acid, the disodium salt of 3,5-pyrocatecholdisulfonic acid, 2,3-dihydroxynaphthalene, and 2,3-dihydroxynaphthalene sulfonyl acid derivatives, and said analogue is selected from the group consisting of EDTA analogues and HEDTA analogues which contain a functional group for binding to an antibody, an antigen, or a hapten.

10. Method according to claim 1 or 9 wherein said analogue is 1-(p-diazoniumphenyl)ethylenediaminetetraacetic acid.

11. Method according to claim 1 or 9 wherein said chelate is a 1:1:1 chelate of said fluorescence emission source, said β-diketone, and said analogue.

12. Method according to claim 11 wherein said β-diketone is selected from the group consisting of thenoyltrifluoroacetone, benzoyltrifluoroacetone, hexafluoroacetylacetone, acetylacetone, and 1- and 2-naphthoyltrifluoroacetone.

13. Method according to claim 1 or 9 wherein said fluorescence emission source is bound to an antibody, an antigen or a hapten molecule via the functional group of said analogue and then said β-ketone or said dihydroxy compound is added to form the 1:1:1 chelate.

14. Method according to claim 13 wherein a β-diketone is added in an excess amount.

15. Method according to claim 1 wherein the fluorescence is measured on a solid.

16. Method according to claim 1 wherein the fluorescence is measured in a solution.

17. In a method for the fluoroimmunoassay of a substance by means of fluorescence spectroscopy in which a fluorescent marker is coupled to the molecules of the substance, the fluorescence of the marker having a duration which substantially exceeds the duration of the fluorescence of possible noise sources and in which the substance is excited by means of a short pulse of radiation and the fluorescence thereby generated is detected when the fluorescence from the sources of noise has in principle ceased, the improvement comprising using as said fluorescent marker a 1:1:1 fluorescent chelate of europium or terbium, a β-diketone or a dihydroxy compound, and an aminopolycarboxylic acid analogue, said chelate having a stability constant above $10^{10}$ wherein (a) the europium or terbium is the fluorescence emission source and is chelated to the aminopolycarboxylic acid analogue, (b) the aminopolycarboxylic acid has a functional group for covalent binding to said substance, (c) said β-diketone is selected from the group consisting of benzoylacetone, dibenzoylmethane, thenoyltrifluoroacetone, benzoyltrifluoroacetone, 1- and 2-naphthoyltrifluoroacetone, acetylacetone, trifluoroacetylacetone, and hexafluoroacetylacetone, (d) said dihydroxy compound is selected from the group consisting of sulphosalicylic acid, the disodium salt of 3,5-pyrocatecholdisulfonic acid, 2,3-dihydroxynaphthalene, and 2,3-dihydroxynaphthalene sulfonyl acid derivatives, and (e) the fluorescent 1:1:1 structure bound to the substance is formed in the presence of said β-diketone or said dihydroxy compound.

18. Method according to claim 17 wherein said analogue is 1-(p-diazoniumphenyl)ethylenediaminetetraacetic acid.

* * * * *

Notice of Adverse Decision in Interference

In Interference No. 101,990, involving Patent No. 4,374,120, E. Soini and I. Hemmila, FLOURESCENCE SPECTROSCOPY ASSAY MEANS WITH FLOURESCENT CHELATE OF A LANTHANIDE, final judgment adverse to the patentees was rendered April 21, 1989, as to claims 1-18.
[*Official Gazette September 19, 1989.*]